(12) United States Patent
Chang (10) Patent No.: US 8,858,570 B2
(45) Date of Patent: Oct. 14, 2014

(54) SKIN TREATMENT APPARATUS

(75) Inventor: Henry Ping Chang, San Marino, CA (US)

(73) Assignees: Henry Ping Chang, San Marino, CA (US); Franklin Chang, San Gabriel, CA (US); Tsung Chang Chang, Taipei (TW)

( * ) Notice: Subject to any disclaimer, the term of this patent is extended or adjusted under 35 U.S.C. 154(b) by 0 days.

(21) Appl. No.: 13/552,657

(22) Filed: Jul. 19, 2012

(65) Prior Publication Data

US 2014/0025090 A1    Jan. 23, 2014

(51) Int. Cl.
*A61B 17/50* (2006.01)

(52) U.S. Cl.
USPC ............................... 606/131; 606/9; 604/289

(58) Field of Classification Search
USPC ..................... 606/9, 131; 604/289
See application file for complete search history.

(56) References Cited

U.S. PATENT DOCUMENTS

| | | | |
|---|---|---|---|
| 6,511,486 B2 * | 1/2003 | Mercier et al. | 606/131 |
| RE42,960 E * | 11/2011 | Waldron | 606/131 |
| 8,343,116 B2 * | 1/2013 | Ignon et al. | 604/289 |
| 2001/0037118 A1 * | 11/2001 | Shadduck | 606/131 |
| 2002/0040229 A1 * | 4/2002 | Norman | 606/180 |
| 2003/0195542 A1 * | 10/2003 | Lee | 606/186 |
| 2004/0138680 A1 * | 7/2004 | Twitchell et al. | 606/131 |
| 2006/0106363 A1 * | 5/2006 | Aravena et al. | 604/506 |
| 2009/0222024 A1 * | 9/2009 | Naldoni | 606/131 |

* cited by examiner

*Primary Examiner* — Darwin Erezo
*Assistant Examiner* — Diane Yabut
(74) *Attorney, Agent, or Firm* — Bacon & Thomas, PLLC (57) ABSTRACT

A skin treatment apparatus includes a handle body, a driving unit received in a receiving cavity of the handle body, a treatment head unit, and an inlet arrangement. The treatment head unit includes a supporting member provided at the front end portion of the handle body, a treatment cap detachably attached on the supporting member, a treatment shaft rotatably connected to the driving unit and extended from the driving unit into a treatment cavity, and an abrasion head integrally formed at a free end of the treatment shaft in such a manner that when the treatment shaft is driven to rotate, the abrasion head is also driven to rotate with respect to the handle body. The inlet arrangement is formed at the supporting member of the treatment head unit for providing a predetermined amount of skin treatment fluid in the treatment cavity.

16 Claims, 5 Drawing Sheets

SKIN TREATMENT APPARATUS

FIELD OF INVENTION

The present invention relates to skin treatment, and more particularly to a skin treatment apparatus which is capable of performing micro-dermabrasion to a user's skin, so as to allow the user's skin to regenerate for cosmetic purpose.

DESCRIPTION OF RELATED ARTS

A conventional skin treatment system, such as a skin treatment system for performing dermabrasion skin treatment, usually comprises a skin treatment apparatus, a fluid reservoir connected to the skin treatment apparatus, a vacuum reservoir also connected to the skin treatment apparatus, and a vacuum source connected to the vacuum reservoir for vacuuming the skin surface during the course of the treatment. The connections between the skin treatment apparatus, the vacuum reservoir, and the fluid reservoir are accomplished by a plurality of tubes which are responsible for transmitting fluid and air so as to form a vacuum loop within the skin treatment system.

The skin treatment apparatus usually comprises a handle body and a skin treatment head formed at a front end portion of the handle body, wherein a user is able to manually hold the handle body and contact the skin treatment head with a predetermined skin area for performing abrasive or any other skin treatment. Very often, the tubes connecting the skin treatment apparatus with the vacuum reservoir and/or the fluid reservoir are attached on the skin treatment apparatus at a position in the vicinity of the skin treatment head.

This brings a problem when a user is manually holding the skin treatment apparatus for performing a skin treatment procedure because the tubes attached on the skin treatment head are likely to hinder a free movement thereof and the user is unable to freely move the skin treatment head on a predetermined skin. When the skin treatment apparatus moves over an extended distance on the skin, the tubes may entangle with each other and this adversely affect the supply of fluids and the formation of the vacuum condition within the skin treatment system.

Moreover, conventional skin treatment system usually does not have accurate and visible indications as to the pressure level developed within the skin treatment system when it is operated to perform a skin treatment procedure. Thus, it is hard for a user or operator of the conventional skin treatment system to manually observe a pressure developed within the vacuum loop and make a corresponding adjustment.

SUMMARY OF THE PRESENT INVENTION

The invention is advantageous in that it provides a skin treatment apparatus in which the fluid inlets are formed at a distance from the handle body so that when a user is performing a skin treatment procedure, the treatment head is not interfered by the fluid inlets and the tubes attaching thereto.

Another advantage of the invention is to provide a skin treatment apparatus in which a user is able to manually hold the handle body for freely performing skin treatment without entangling the tubes transmitting fluids to and from the skin treatment apparatus.

Another advantage of the invention is to provide a skin treatment apparatus in which is capable of performing dermabrasion skin treatment in an optimal manner in the sense that the abrasion can be stably performed at a very low rotational speed by a treatment head.

Another advantage of the invention is to provide a skin treatment system comprising the skin treatment apparatus in which a user is able to monitor and adjust a pressure developed within the skin treatment system so as to optimize and fully control the skin treatment procedure.

Another advantage of the invention is to provide a skin treatment apparatus comprising a treatment head which is capable of defining a vacuum treatment chamber for effectively circulating a predetermined amount of skin treatment fluid so as to maximize an efficiency and effectiveness of the corresponding skin treatment procedure.

Additional advantages and features of the invention will become apparent from the description which follows, and may be realized by means of the instrumentalities and combinations particular point out in the appended claims.

According to the present invention, the foregoing and other objects and advantages are attained by providing a skin treatment apparatus, comprising:

a handle body having a front end portion, a rear end portion, and a receiving cavity formed between the front end portion and the rear end portion;

a driving unit received in the receiving cavity of the handle body;

a treatment head unit, which comprises:

a supporting member provided at the front end portion of the handle body;

a treatment cap detachably attached on the supporting member to form a treatment cavity between the supporting member and the treatment cap, wherein the treatment cap has a through cap opening formed thereon;

a treatment shaft rotatably connected to the driving unit and extended from the driving unit into the treatment cavity;

an abrasion head integrally formed at a free end of the treatment shaft in such a manner that when the treatment shaft is driven to rotate, the abrasion head is also driven to rotate with respect to the handle body, wherein a length of the treatment shaft and the abrasion head is slightly shorter than a length of the treatment cap so as to form a treatment gap defined between the abrasion head and the cap opening; and an inlet arrangement, which comprises a fluid inlet and a vacuum inlet formed at the supporting member of the treatment head unit for providing a predetermined amount of skin treatment fluid in the treatment cavity, wherein the inlet arrangement is arranged to generate a vacuum effect in the treatment cavity so that the skin treatment fluid is capable of being effectively and efficiently delivered to and sucked out of the treatment cavity while the abrasion head operates to treat user's skin.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
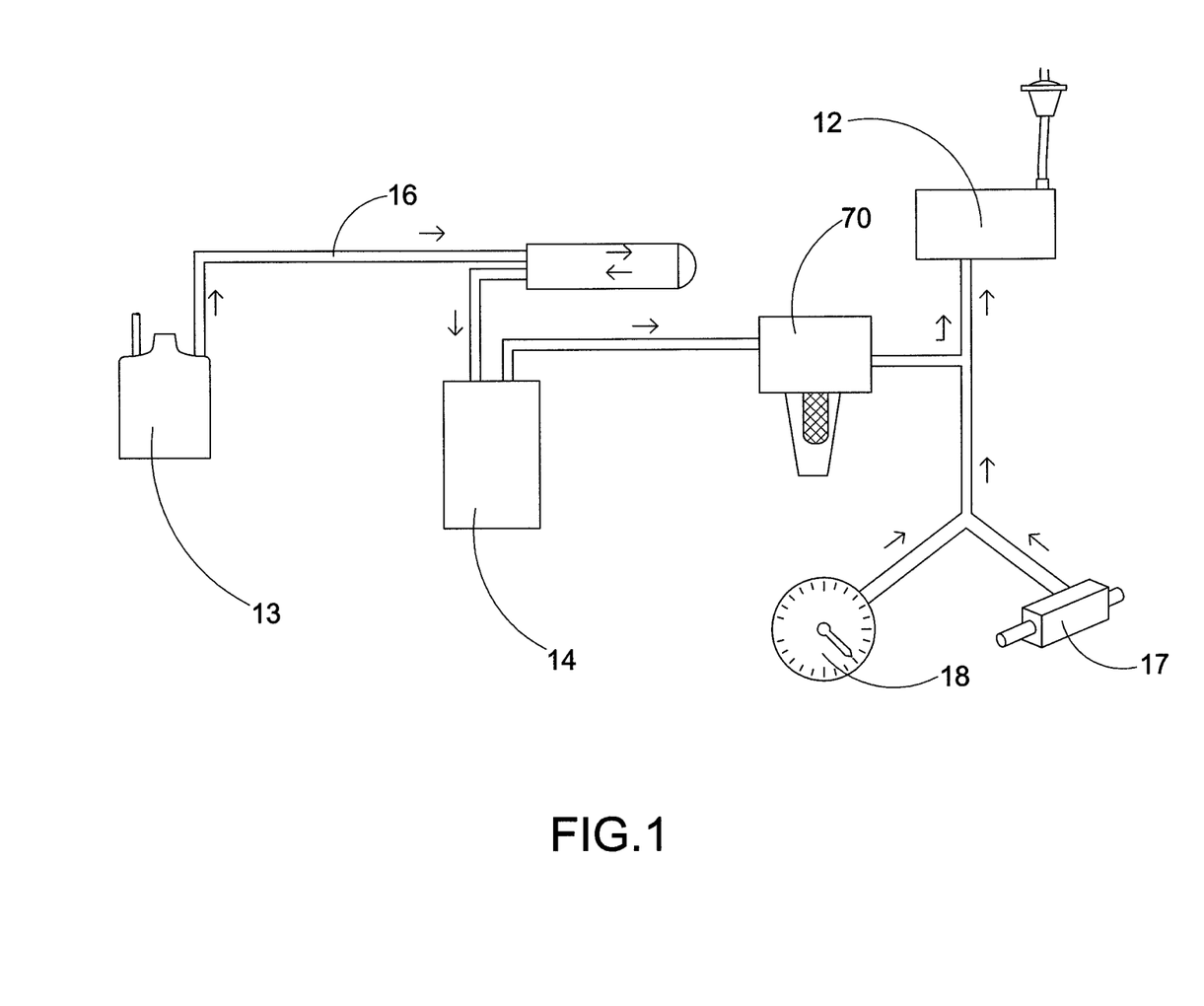
FIG. 1 is a schematic diagram of a skin treatment system according to a preferred embodiment of the present invention.
Figure 5:
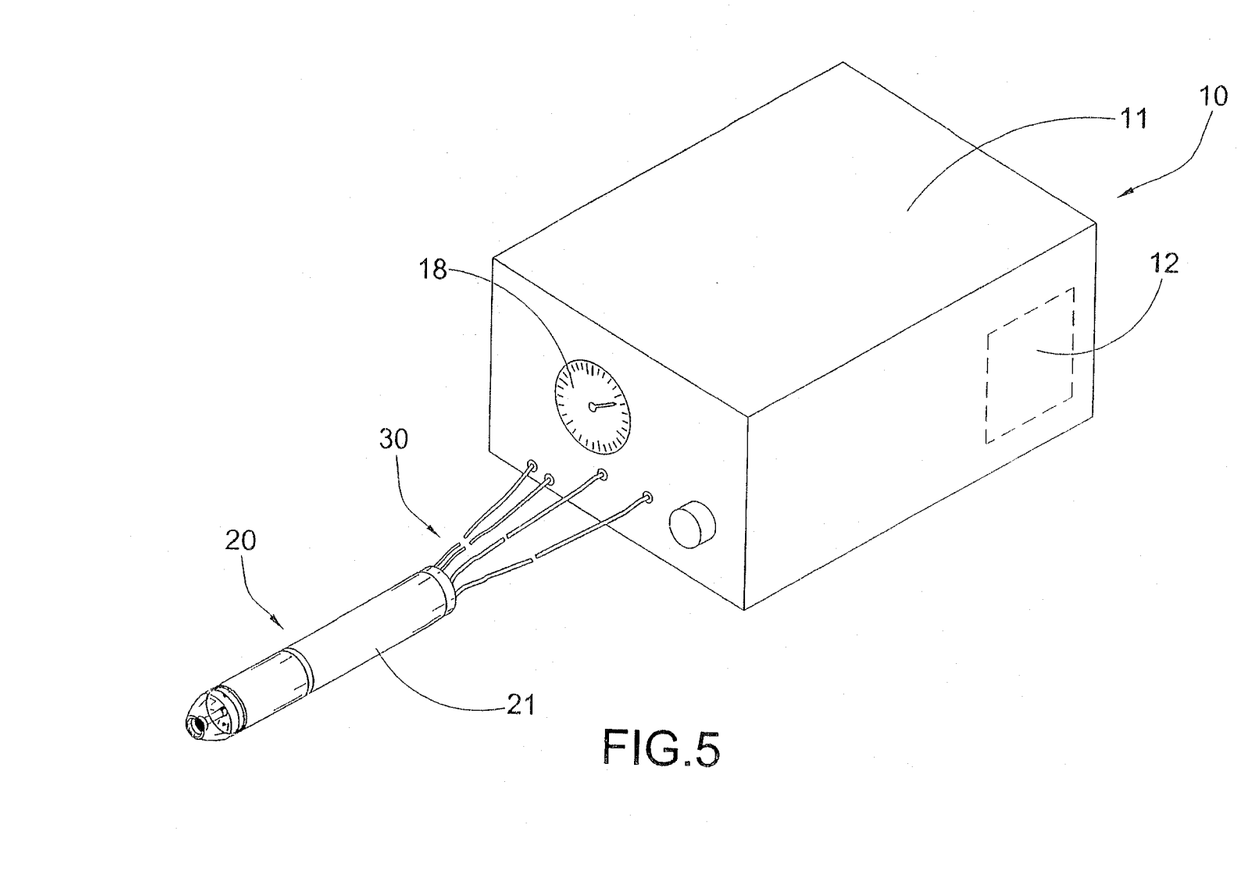
FIG. 5 is a schematic diagram of the skin treatment system according to the above preferred embodiment of the present invention.

Referring to FIG. 1 and FIG. 5 of the drawings, a skin treatment system according to a preferred embodiment of the present invention is illustrated, in which the skin treatment system comprises a main unit 10, a skin treatment apparatus 20 extended from the main unit 10 for performing skin treatment on a predetermined skin area, and an inlet arrangement 30.

The main unit 10 comprises a main housing 11, a vacuum source such as a pump 12 mounted in the main housing 10, a fluid reservoir 13 mounted in the main housing 11 for containing a predetermined amount of fluid used for skin treatment purpose, a waste reservoir 14 also mounted in the main housing 11 for collecting fluid waste caused by the skin treatment, and a plurality of transmission tubes 16 connecting the fluid reservoir 13, the skin treatment apparatus 20, and the waste reservoir 14 in a predetermined manner for forming a skin treatment loop within the skin treatment system.

Figure 2:
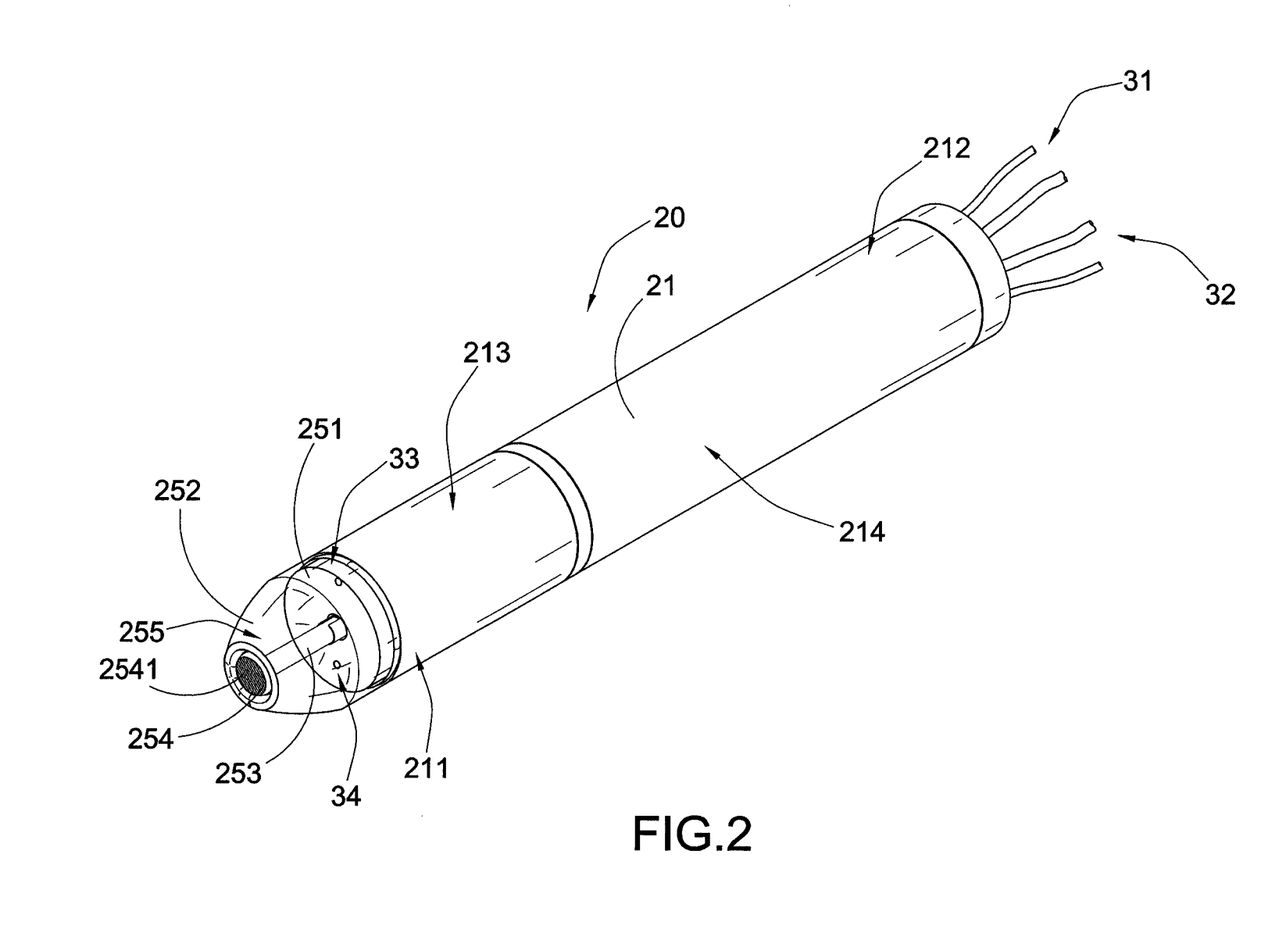
FIG. 2 is a perspective view of a skin treatment apparatus according to the above preferred embodiment of the present invention.
Figure 3:
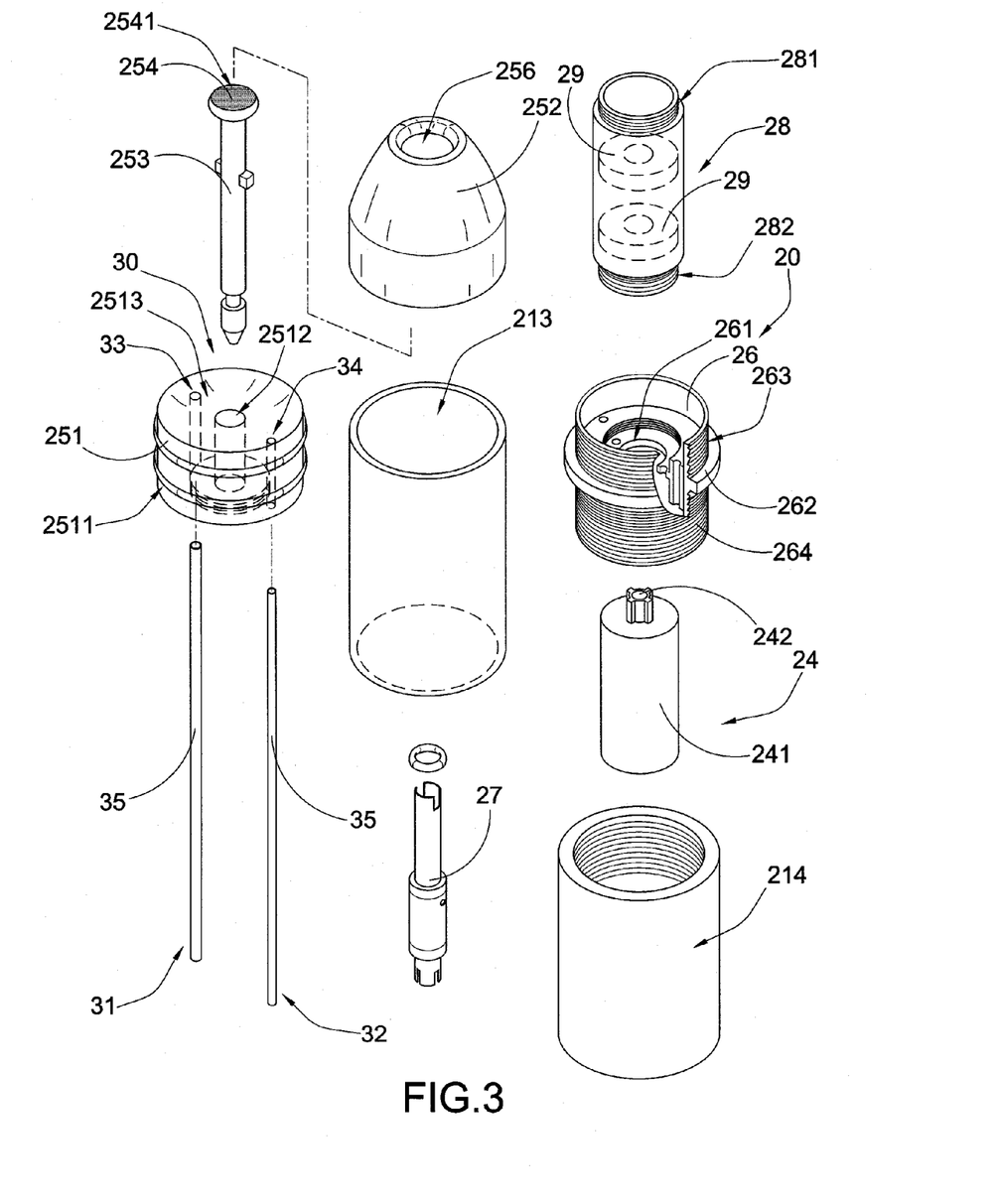
FIG. 3 is an exploded perspective view of the skin treatment apparatus according to the above preferred embodiment of the present invention.
Figure 4:
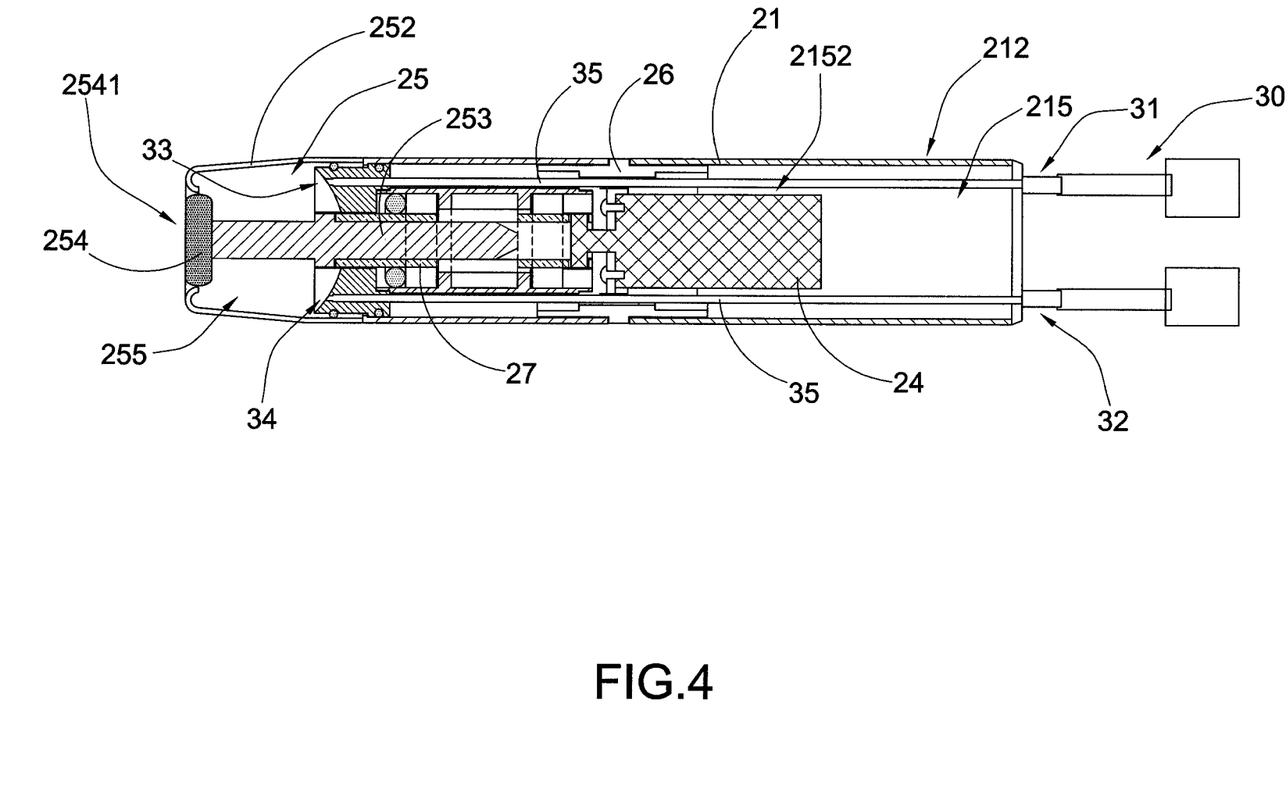
FIG. 4 is a sectional side view of the skin treatment apparatus according to the above preferred embodiment of the present invention.

On the other hand, the skin treatment apparatus 20 comprises a handle body 21 having a front end portion 211, a rear end portion 212, and a receiving cavity 215 formed between the front end portion 211 and the rear end portion 212. Furthermore, the skin treatment apparatus 20 further comprises a driving unit 24, and a treatment head unit 25. The driving unit 24 is received in the receiving cavity 215 of the handle body 21. The treatment head unit 25 comprises a supporting member 251, a treatment cap 252, a treatment shaft 253, and an abrasion head 254.

The supporting member 251 is provided at the front end portion 211 of the handle body 21, while the treatment cap 252 is detachably attached on the supporting member 251 to form a treatment cavity 255 between the supporting member 251 and the treatment cap 252, wherein the treatment cap 252 has a through cap opening 256 formed thereon.

The treatment shaft 253 is rotatably connected to the driving unit 24 and extended from the driving unit 24 into the treatment cavity 255.

The abrasion head 254 is integrally formed at a free end of the treatment shaft 253 in such a manner that when the treatment shaft 253 is driven to rotate, the abrasion to head 254 is also driven to rotate with respect to the handle body 21, wherein a length of the treatment shaft 253 and the abrasion head 254 is slightly shorter than a length of the treatment cap 252 so as to form a treatment gap defined between the abrasion head 254 and the cap opening 256.

The an inlet arrangement 30, which comprises a fluid inlet 31 and a vacuum inlet 32 formed the rear end portion 212 of the handle body 21 for providing a predetermined amount of skin treatment fluid in the treatment cavity 255, wherein the inlet arrangement 30 is arranged to generate a vacuum effect in the treatment cavity 255 so that the skin treatment fluid is capable of being effectively and efficiently delivered to and sucked out of the treatment cavity 255 while the abrasion head 254 operates to treat user's skin.

According to the preferred embodiment of the present invention, the skin treatment apparatus further comprises a securing member 26 mounted in the receiving cavity 215 of the handle body 21 for securely mounting the driving unit 24 within the receiving cavity 215. More specifically, and as shown in FIG. 3 of the drawings, the securing member 26 has a tubular structure and has a through hole 261 formed thereon for allowing the treatment shaft 253 of the treatment head unit 25 to pass therethrough. In other words, the securing member 26 is mounted in the receiving cavity 215 of the handle body 21 to define the receiving cavity 215 in a front receiving portion 2151 and a rear receiving portion 2152, wherein the driving unit 24 is accommodated in the rear receiving portion 2152, while the treatment shaft 253 is extended from the driving unit 24 to the first receiving portion 2151 through the securing member 26.

Moreover, the handle body 21 further comprises a front body part 213 and a rear body part 214, wherein the front end portion 211 is formed on the front body part 213 while the rear end portion 212 is formed on the rear body part 214 respectively. The securing member 26 has an outer circumferential ridge 262 outwardly protruded from a mid portion thereof to divide the securing member 26 into a first connecting portion 263 and a second connecting portion 264, wherein an external surface of each of the first connecting portion 263 and the second connecting portion 264 are threaded to connect with the handle body 21.

Thus, the front body part 213 is threadedly connected to the first connecting portion 263 of the securing member 26 while the rear body part 214 is threadedly connected to the second connecting portion 264 of the securing member 26. It is worth mentioning that in order to maintain a secure connection between the securing member 26 and the handle body 21, the securing member 26 is preferably made of metallic material so as to ensure sufficient material strength thereof.

On the other hand, the supporting member 251 has a circular cross section and is preferably made of plastic material. Moreover, the supporting member 251 further has a plurality of peripheral rims 2511 outwardly and circumferentially protruded from an outer surface of the supporting member 251, wherein the front body part 213 of the handle body 214 is connected to the supporting member 251 at the corresponding peripheral rim 2511. Note that the peripheral rims 2511 may be embodied as O-rings attached on the supporting member 251.

Note also that the supporting member 251 further has a central through slot 2512 formed thereon, wherein the treatment shaft 253 is arranged to extend from the receiving cavity 215 to the treatment cavity 255 through the central through slot 2512.

Moreover, the supporting member 251 has a concave front surface 2513 wherein the central through slot 2512 is formed on the concave front surface 2513. The provision of the concave front surface 2513 serves to maximize the volume of the treatment cavity 255 and to enable a more effective and efficient vacuum effect to be formed in the treatment cavity 255.

The fluid inlet 31 and a vacuum inlet 32 are formed at the rear end portion 212 of the handle body 21 (i.e. the rear body part 214), wherein the inlet arrangement 30 further has a fluid outlet 33 and a vacuum outlet 34 spacedly formed on the concave front surface 2513 of the supporting member 251. Moreover, the inlet arrangement 30 further comprises a plurality of fluid passage tubes 35 extended between the fluid inlet 31 and the fluid outlet 33, and between the vacuum 32 and the vacuum outlet 34 respectively.

According to the preferred embodiment of the present invention, the main unit 10 further comprises a pressure gauge 18 provided on the main housing 10, wherein the pressure gauge 18 has a plurality of unit indicators 19 formed thereon for allowing a user to discern a current pressure and vacuum level of the skin treatment system. As such, the user is able to monitor the treatment status in a real-time manner. Note that the pressure gauge 18 is connected to the fluid reservoir 13 and the waste reservoir 14 for monitoring the pressure level of the skin treatment system. Moreover, the skin treatment system further comprises an adjustment switch 17 connected to the pump 12 and the pressure gauge 18 for adjusting a fluid flow in the skin treatment system.

The fluid reservoir 13 is mounted in the main housing 11 and is arranged to contain a predetermined amount of treatment fluid and optionally a predetermined amount of abrasive materials, wherein when the pump 12 is activated to create a vacuum effect in the skin treatment system, the treatment fluid is pumped to the skin treatment apparatus and reaches the skin surface through the fluid outlet 33 provided at the treatment head unit 25.

The skin treatment system further comprises a filter unit 70 provided in-line in between the pump 12 and the waste reservoir 14 so as to ensure the vacuum source is substantially protected against dirt from collected in the waste reservoir 14. The filter unit 70 may be an in-line condensation filter, or other suitable filter.

The driving motor 24 comprises a motor body 241 mounted in the receiving cavity 215 of the handle body 21, and a driving shaft 242 extended from the motor body 241 to extend in the receiving cavity 215. Moreover, the skin treatment apparatus 20 further comprises a connecting shaft 27 connecting the driving shaft 242 to the treatment shaft 253 in such a manner that when the driving shaft 242 is driven to rotate, the connecting shaft 27 is also driven to rotate and is arranged to drive the treatment shaft 253 to rotate as well so as to allow the abrasion head 254 to perform skin treatment to the user's skin.

Moreover, the skin treatment apparatus 20 further comprises a protective tube 28 having two end portions 281, 282 which are threaded on an external surface thereof. The corresponding end portion 281 is arranged to connect to the securing member 26. Moreover, the skin treatment apparatus 20 further comprises a plurality of ball bearings 29 provided in the protective tube 28, wherein the connecting shaft 27 is arranged to penetrate and is protected by the protective tube 28. Thus, the connecting shaft 27 is arranged to penetrate through and is supported by the ball bearings 29.

The abrasion head 254 has a circular cross section and has an abrasive surface 2541 formed thereon, wherein the abrasion surface 2541 is aligned with the through cap opening 256 so as to perform skin treatment to the user's skin when the skin is disposed at the cap opening 256.

Note that by contacting the rotating abrasion head 254 and the user's skin, the outer dead skin of the user can be effectively removed and this makes the user's skin to be cosmetically fresh and superior.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A skin treatment system, comprising a skin treatment apparatus which comprises a handle body and a treatment head unit, wherein said handle body has a front end portion, a rear end portion, and a receiving cavity formed between said front end portion and said rear end portion, wherein said treatment head unit comprises a supporting member, a treatment shaft, an abrasion head, and an inlet arrangement, wherein a driving motor comprises a motor body mounted in said receiving cavity of said handle body, a driving shaft extending from said motor body to said receiving cavity, and a connecting shaft connecting said driving shaft to said treatment shaft, wherein said supporting member is removably mounted in said receiving cavity, and said supporting member has a central through slot for supporting the treatment shaft, wherein said treatment shaft is rotatably driven by said driving motor and is forwardly extended from said driving motor through said central through slot of said supporting member, wherein said abrasion head is integrated at a free end of said treatment shaft so that when said treatment shaft is driven to rotate, said abrasion head is also driven to rotate, wherein said inlet arrangement comprises a fluid outlet and a vacuum outlet spacedly formed at a front surface of said supporting member, a fluid inlet and a vacuum inlet formed at said rear end portion of said handle body, and a plurality of fluid passage tubes extended from said fluid inlet and said vacuum inlet to said fluid outlet and said vacuum outlet respectively through said supporting member, so that said supporting member supports and retains said treatment shaft and said fluid passage tubes in said receiving cavity, wherein a plurality of ball bearings are provided in a protective tube, and the connecting shaft is supported and protected in the protective tube by penetrating through the ball bearings therein;

wherein a securing member is mounted in said receiving cavity of said handle body for securing said driving motor in said receiving cavity, wherein said securing member has a tubular structure and has a through hole aligned with said central through slot of said supporting member and defines a front receiving portion and a rear receiving portion, wherein said driving motor is accommodated in said rear receiving portion, and said treatment shaft extends from said driving motor to said front end portion of said handle body through said through hole of said securing member and said central through slot of said supporting member;

wherein said handle body further comprises a front body part and a rear body part, wherein said front end portion is formed on said front body part while said rear end portion is formed on said rear body part respectively, wherein said securing member has an outer circumferential ridge outwardly protruded from a mid portion thereof to divide said securing member into a first connecting portion and a second connecting portion, wherein an external surface of each of said first connecting portion and said second connecting portion are threaded to connect with said handle body.

2. The skin treatment system of claim 1, wherein said front surface of said supporting member is a concave front surface forming a treatment cavity in front of said concave front surface at said front end portion of said handle body, so that said fluid outlet and said vacuum outlet are spacedly formed at said concave front surface of said supporting member.

3. The skin treatment system of claim 2, wherein said supporting member further has a plurality of peripheral rims outwardly and circumferentially protruded from an outer surface of said supporting member, wherein said front body part of said handle body is connected to at least one of the peripheral rims of said supporting member.

4. The skin treatment system of claim 3, further comprising a main unit, which comprises a main housing, a vacuum source in said main housing to link with said vacuum inlet, a fluid reservoir mounted in said main housing for containing a predetermined amount of skin treatment fluid, and a waste reservoir mounted in said main housing for collecting fluid waste from said vacuum outlet.

5. The skin treatment system of claim 4, wherein said main unit further comprises a plurality of transmission tubes connecting said fluid reservoir, said skin treatment apparatus and said waste reservoir in a predetermined manner for forming a skin treatment loop within said skin treatment system.

6. The skin treatment system of claim 1, further comprising a main unit, which comprises a main housing, a vacuum source in said main housing to link with said vacuum inlet, a fluid reservoir mounted in said main housing for containing a predetermined amount of skin treatment fluid, and a waste reservoir mounted in said main housing for collecting fluid waste from said vacuum outlet.

7. The skin treatment system of claim 6, wherein said main unit further comprises a plurality of transmission tubes connecting said fluid reservoir, said skin treatment apparatus and said waste reservoir in a predetermined manner for forming a skin treatment loop within said skin treatment system.

8. A skin treatment apparatus, comprising:
a handle body, having a front end portion, a rear end portion, and a receiving cavity formed between said front end portion and said rear end portion;
a treatment head unit, having a supporting member provided at said front end portion of said handle body and removably mounted in said receiving cavity; a treatment cap detachably attached on said supporting member to form a treatment cavity between said supporting member and said treatment cap, wherein said treatment cap has a through cap opening formed thereon; a treatment shaft rotatably connected to a driving unit and extended from said driving unit into said treatment cavity, wherein said supporting member has a central through slot for supporting the treatment shaft, and wherein said treatment shaft is arranged to extend from said receiving cavity to said treatment cavity through said central through slot; said driving unit comprising a motor body mounted in said receiving cavity of said handle body, and a driving shaft extended from said motor body to extend in said receiving cavity; an abrasion head integrally formed at a free end of said treatment shaft in such a manner that when said treatment shaft is driven to rotate, said abrasion head is also driven to rotate with respect to said handle body, wherein a length of said treatment shaft and said abrasion head within said treatment cavity is slightly shorter than a length of said treatment cap so as to form a treatment gap defined between said abrasion head and said cap opening; and an inlet arrangement, which comprises a fluid inlet and a vacuum inlet formed at a rear end portion of said handle body for providing a predetermined amount of skin treatment fluid in said treatment cavity, wherein said inlet arrangement is arranged to generate a vacuum effect in said treatment cavity so that said skin treatment fluid is capable of being effectively and efficiently delivered to and sucked out of said treatment cavity while said abrasion head operates to treat user's skin; and
a connecting shaft connecting said driving shaft to said treatment shaft in such a manner that when said driving shaft is driven to rotate, said connecting shaft is also driven to rotate and is arranged to drive said treatment shaft to rotate as well so as to allow said abrasion head to perform skin treatment to user's skin, wherein a plurality of ball bearings are provided in a protective tube, and the connecting shaft is supported and protected in the protective tube by penetrating through the ball bearings therein;
wherein said driving unit is received in said receiving cavity of said handle body, and a securing member is mounted in said receiving cavity of said handle body for securely mounting said driving unit within said receiving cavity; and
wherein said securing member has a tubular structure and has a through hole formed thereon for allowing said treatment shaft of said treatment head unit to pass therethrough, in such a manner that said securing member is mounted in said receiving cavity of said handle body to define said receiving cavity into a front receiving portion and a rear receiving portion, wherein said driving unit is accommodated in said rear receiving portion, while said treatment shaft is extended from said driving unit to said front receiving portion through said securing member.

9. The skin treatment apparatus of claim 8, wherein said handle body further comprises a front body part and a rear body part, wherein said front end portion is formed on said front body part while said rear end portion is formed on said rear body part respectively, wherein said securing member has an outer circumferential ridge outwardly protruded from a mid portion thereof to divide said securing member into a first connecting portion and a second connecting portion, wherein an external surface of each of said first connecting portion and said second connecting portion are threaded to connect with said handle body.

10. The skin treatment apparatus of claim 9, wherein said supporting member further has a plurality of peripheral rims outwardly and circumferentially protruded from an outer surface of said supporting member, wherein said front body part of said handle body is connected to at least one of the peripheral rims of said supporting member.

11. The skin treatment apparatus of claim 10, wherein said supporting member has a concave front surface, wherein said central through slot is formed on said concave front surface for maximizing a volume of said treatment cavity and to enable a more effective and efficient vacuum effect to be formed in said treatment cavity.

12. The skin treatment apparatus of claim 11, wherein said inlet arrangement further has a fluid outlet and a vacuum outlet spacedly formed on said concave front surface of said supporting member, wherein said inlet arrangement further comprises a plurality of fluid passage tubes extended between said fluid inlet and said fluid outlet, and between said vacuum inlet and said vacuum outlet, respectively, for transmission of skin treatment fluid by vacuum effect.

13. The skin treatment apparatus of claim 12, wherein said abrasion head has a circular cross section and has an abrasive surface formed thereon, and said abrasion surface is aligned with said through cap opening so as to perform skin treatment to said user's skin when said skin is disposed at said cap opening.

14. A skin treatment system, comprising a skin treatment apparatus which comprises:
a handle body having a front end portion, a rear end portion, and a receiving cavity formed between said front and rear end portions;
a driving unit received in the receiving cavity of the handle body;

a treatment head unit comprising a supporting member provided at the front end portion of the handle body, a treatment cap detachably attached on the supporting member to form a treatment cavity between the supporting member and the treatment cap, wherein the treatment cap has a through cap opening formed thereon, a treatment shaft rotatably connected to the driving unit and extended from the driving unit into the treatment cavity, an abrasion head integrally formed at a free end of the treatment shaft such that the abrasion head is driven to rotate when the treatment shaft is driven to rotate, and an inlet arrangement for providing a skin treatment fluid in the treatment cavity;

wherein said supporting member has a central through slot and is removably mounted in said receiving cavity;

wherein said treatment shaft is rotatably driven by said driving unit and is forwardly extended from said driving unit through said central through slot of said supporting member;

wherein the handle body further comprises a front body part detachably connected to a rear body part by a securing member mounted in the receiving cavity for securely mounting the driving unit within the receiving cavity, such that the front end portion is formed on the front body part and the rear end portion is formed on the rear body part;

wherein the securing member defines a first connecting portion for removably connecting to the front body part, a second connecting portion for removably connecting to the rear body part, an outer circumferential ridge located between the first and second connecting portions and outwardly protruding therefrom such that the front and rear body parts do not contact each other when secured to the securing member, and a through hole for allowing the treatment shaft to pass therethrough;

wherein said driving unit comprises a motor body mounted in said receiving cavity of said handle body, a driving shaft extending from said motor body to said receiving cavity, and a connecting shaft connecting said driving shaft to said treatment shaft;

wherein said inlet arrangement comprises a fluid outlet and a vacuum outlet spacedly formed at a front surface of said supporting member, a fluid inlet and a vacuum inlet formed at said rear end portion of said handle body, and a plurality of fluid passage tubes extended from said fluid inlet and said vacuum inlet to said fluid outlet and said vacuum outlet, respectively, through said supporting member, so that said supporting member supports and retains said treatment shaft and said fluid passage tubes in said receiving cavity; and wherein the plurality of fluid passage tubes extend through corresponding holes formed along an inner circumferential ridge of the securing member.

15. The skin treatment system of claim 14, further comprising a protective tube provided in the receiving cavity and having a first end portion removably connected to the supporting member and a second end portion removably connected to the securing member, wherein a plurality of ball bearings are provided in the protective tube for supporting and protecting the connecting shaft; and wherein the securing member mounted in the receiving cavity defines a front receiving portion and a rear receiving portion, such that the driving unit is accommodated in the rear receiving portion while the treatment shaft is extended from the driving unit to the front receiving portion through the securing member.

16. The skin treatment system of claim 14, wherein the skin treatment apparatus is configured to extend from a main housing such that the fluid inlet and the vacuum inlet are in communication with a fluid reservoir mounted in the main housing and a waste reservoir mounted in the main housing, respectively.

\* \* \* \* \*